US00PP24227P2

(12) United States Plant Patent
Wood

(10) Patent No.: US PP24,227 P2
(45) Date of Patent: Feb. 11, 2014

(54) ***VIBURNUM* PLANT NAMED 'REDELL'**

(50) Latin Name: *Viburnum hybrida*
Varietal Denomination: Redell

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 88 days.

(21) Appl. No.: 13/506,508

(22) Filed: Apr. 23, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Viburnum* plant named 'Redell', characterized by its upright and somewhat outwardly spreading plant habit; vigorous growth habit; freely branching habit; numerous white-colored flowers; numerous red-colored fruits arranged in dense clusters; and good garden performance.

2 Drawing Sheets

Botanical designation: *Viburnum hybrida.*
Cultivar denomination: 'REDELL'.

BACKGROUND OF THE INVENTION

The present invention relates to a new and distinct cultivar of *Viburnum* plant, botanically known as *Viburnum hybrida* and hereinafter referred to by the name 'Redell'.

The new *Viburnum* plant is a product of a planned breeding program conducted by the Inventor in Grand Haven, Mich. The objective of the breeding program is to develop new *Viburnum* plants with unique and attractive foliage and flower coloration.

The new *Viburnum* plant originated from an open-pollination in 2001 of *Viburnum burejaeticum*×*Viburnum rhytidophylloides* 'Emerald Triumph', not patented, as the female, or seed, parent with an unknown selection of *Viburnum hybrida*, not patented, as the male, or pollen, parent. The new *Viburnum* plant was discovered and selected by the Inventor in 2008 as a single flowering plant from within the progeny of the stated open-pollination in a controlled environment in Grand Haven, Mich.

Asexual reproduction of the new *Viburnum* plant by softwood cuttings in a controlled environment in Grand Haven, Mich. since the spring of 2009 has shown that the unique features of this new *Viburnum* plant are stable and reproduced true to type in successive generations of asexual reproduction.

SUMMARY OF THE INVENTION

Plants of the new *Viburnum* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Redell'. These characteristics in combination distinguish 'Redell' as a new and distinct *Viburnum* plant:

1. Upright and somewhat outwardly spreading plant habit
2. Vigorous growth habit. .

3. Freely branching habit.
4. Numerous white-colored flowers.
5. Numerous red-colored fruits arranged in dense clusters.
6. Good garden performance.

Plants of the new *Viburnum* can be compared to plants of the female parent, 'Emerald Triumph'. Plants of the new *Viburnum* differ from plants of 'Emerald Triumph' in the following characteristics:

1. Plants of the new *Viburnum* are more compact than plants of 'Emerald Triumph'.
2. Plants of the new *Viburnum* have denser fruit clusters than plants of 'Emerald Triumph'.
3. Fruit color of plants of the new *Viburnum* is more uniform than fruit color of plants of 'Emerald Triumph'.

Plants of the new *Viburnum* can be compared to plants of the *Viburnum lantana* 'Mohican', not patented. Plants of the new *Viburnum* differ from plants of 'Mohican' in the following characteristics:

1. Plants of the new *Viburnum* are more compact than plants of 'Mohican'.
2. Plants of the new *Viburnum* have denser fruit clusters than plants of 'Mohican'.

BRIEF DESCRIPTION OF THE PHOTOGRAPHS

The accompanying colored photographs illustrate the overall appearance of the new *Viburnum* plant showing the colors as true as it is reasonably possible to obtain in colored reproductions of this type. Colors in the photographs may differ slightly from the color values cited in the detailed botanical description which accurately describe the colors of the new *Viburnum* plant.

The photograph on the first sheet is a side perspective view of a typical plant of 'Redell' grown in an outdoor nursery.

The photograph on the second sheet is a close-up view of fruit clusters and leaves of 'Redell'.

DETAILED BOTANICAL DESCRIPTION

The aforementioned photographs and following observations, measurements and values describe plants of the new

*Viburnum* grown during the spring in ground beds in an outdoor nursery in Grand Haven, Mich. and under cultural practices which closely approximate commercial *Viburnum* production. Plants were one year old when the photographs and the description were taken. In the description, color references are made to The Royal Horticultural Society Colour Chart, 1995 Edition, except where general terms of ordinary dictionary significance are used.

Botanical classification: *Viburnum hybrida* 'Redell'.

Parentage:

*Female, or seed, parent.*—*Viburnum burejaeticum*× *Viburnum rhytidophylloides* 'Emerald Triumph', not patented.

*Male, or pollen, parent.*—Unknown selection of *Viburnum hybrida*, not patented.

Propagation:

*Type.*—By softwood cuttings.

*Time to initiate roots, summer.*—About 20 days at 25° C.

*Time to produce a rooted young plant, summer.*—About three months at 25° C.

*Root description.*—Fine to thick, fibrous.

*Rooting habit.*—Freely branching; dense.

Plant description:

*Plant and growth habit.*—Deciduous perennial shrub; upright and somewhat outwardly spreading plant habit; vigorous growth habit.

*Branching habit.*—Freely branching habit with numerous primary lateral branches; pinching (removal of terminal apices) will enhance lateral branch development.

*Plant height.*—About 100 cm to 150 cm.

*Plant diameter* (*area of spread*).—About 75 cm to 100 cm.

Lateral branch description:

*Length.*—About 25 cm.

*Diameter.*—About 6 mm.

*Internode length.*—About 6.5 cm.

*Texture.*—Developing stems, pubescent; developed stems, smooth, glabrous.

*Strength.*—Strong.

*Aspect.*—Erect to about 30° from vertical.

*Color, developing.*—Close to 147D.

*Color, developed.*—Close to 197B.

Foliage description:

*Arrangement.*—Opposite, simple.

*Length.*—About 12 cm.

*Width.*—About 7.5 cm.

*Shape.*—Ovate.

*Apex.*—Acute.

*Base.*—Cordate.

*Margin.*—Serrate.

*Texture, upper and lower surfaces.*—Pubescent.

*Venation pattern.*—Pinnate.

*Color.*—Developing leaves, upper surface: Close to 143A. Developing leaves, lower surface: Close to 148C. Fully expanded leaves, upper surface: Close to 141B; venation, close to 151 A. Fully expanded leaves, lower surface: Close to 137C; venation, close to 148D.

*Petiole.*—Length: About 1.5 cm. Diameter: About 3 mm. Texture, upper and lower surfaces: Smooth, glabrous. Color, upper and lower surfaces: Close to 148C.

Flower description:

*Flower appearance and arrangement.*—Single salverform flowers arranged in terminal cymes; freely flowering habit with usually about 62.5 flowers per inflorescence; flowers face upright to outwardly.

*Natural flowering season.*—Continuous flowering during May in Grand Haven, Mich.; flowers last about two to three weeks on the plant; flowers not persistent.

*Fragrance.*—Fragrant; sweet, pleasant.

*Inflorescence height.*—About 8 cm.

*Inflorescence diameter.*—About 11 cm.

*Flower diameter.*—About 9 mm.

*Flower length* (*height*).—About 1.4 cm.

*Flower buds.*—Length: About 3.5 mm. Diameter: About 3.5 mm. Shape: Globose. Color: Close to 157A.

*Petals.*—Quantity per flower: Single whorl of five. Length: About 4 mm. Width: About 3.8 mm. Lobe shape: Broadly ovate. Apex: Acute to obtuse. Margin: Entire. Texture, upper and lower surfaces: Smooth, glabrous. Color: When opening, upper and lower surfaces: Close to 157D. Fully opened, upper and flower surfaces: Close to 155D; color becoming closer to 164B with development.

*Sepals.*—Quantity per flower: Five in a single whorl. Length: About 0.5 mm. Width: About 0.4 mm. Shape: Lanceolate. Apex: Acute. Margin: Entire. Texture, upper and lower surfaces: Smooth, glabrous. Color: When opening, upper and lower surfaces: Close to 145A. Fully opened, upper and lower surfaces: Close to 145A.

*Peduncles.*—Length: About 1.5 cm. Diameter: About 3 mm to 4 mm. Strength: Strong. Angle: About 45° from vertical. Color: Close to 145A.

*Pedicels.*—Length: About 4 mm. Diameter: About 2 mm. Strength: Strong. Angle: About 40° from peduncle axis. Color: Close to 145A.

*Reproductive organs.*—Androecium: Quantity per flower: About five. Anther shape: Globose. Anther length: About 0.5 mm. Anther color: Close to 1B Amount of pollen: Abundant. Pollen color: Close to 1B. Gynoecium: Quantity per flower: One. Pistil length: About 0.8 mm. Style length: About 0.5 mm. Style color: Close to 145A. Stigma color: Close to 145A. Ovary color: Close to 145A.

*Fruits.*—Quantity per lateral branch: About 450 to 600 in dense clusters. Length: About 7 mm. Diameter: About 5 mm. Texture: Smooth, glabrous. Color: Close to between 180A and 42A.

Garden performance: Plants of the new *Viburnum* have been observed to have good garden performance and to tolerate rain, wind and temperatures ranging from about −29° C. to about 37° C.

Pathogen & pest resistance: Plants of the new *Viburnum* have not been observed to be resistant to pathogens and pests common to *Viburnum* plants.

It is claimed:

1. A new and distinct *Viburnum* plant named 'Redell' as illustrated and described.

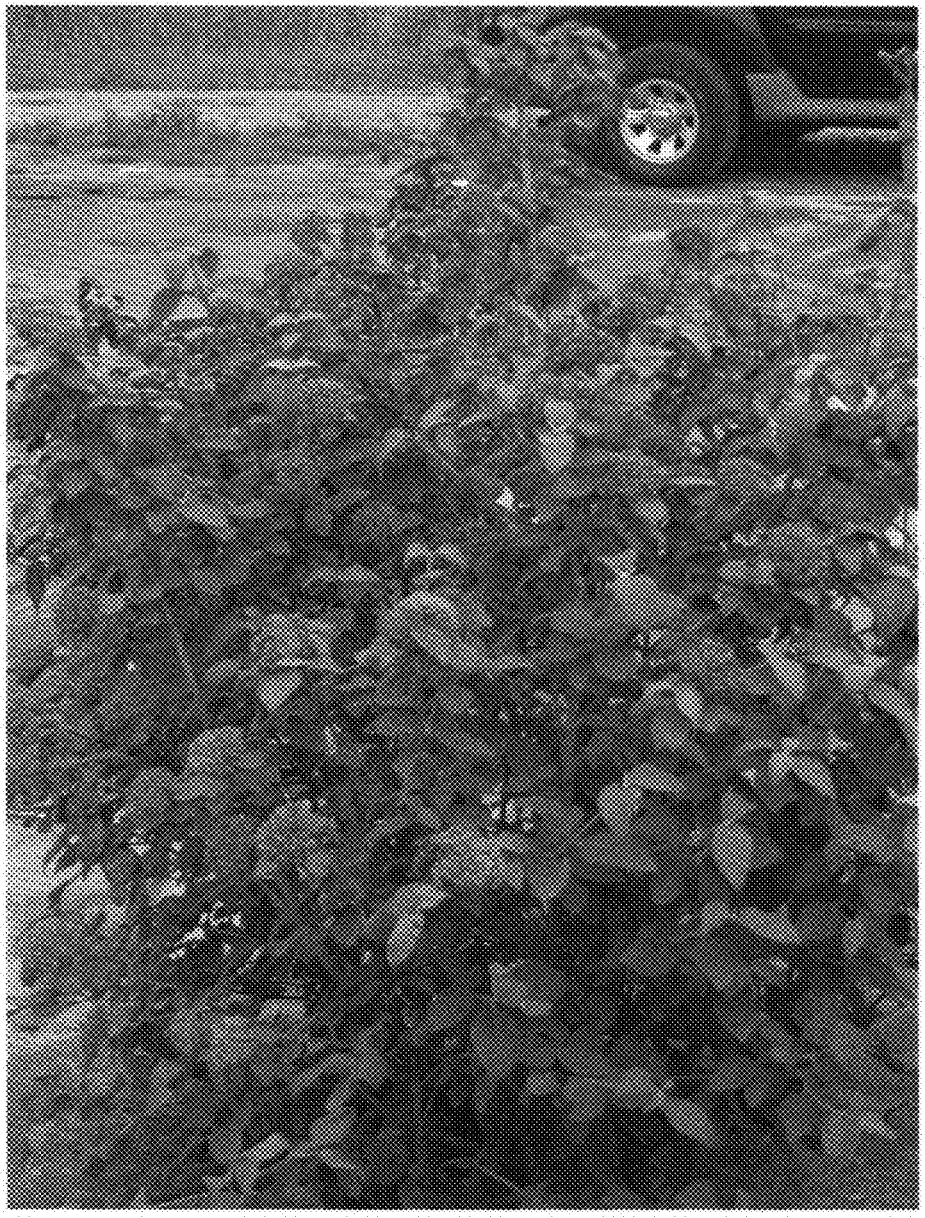

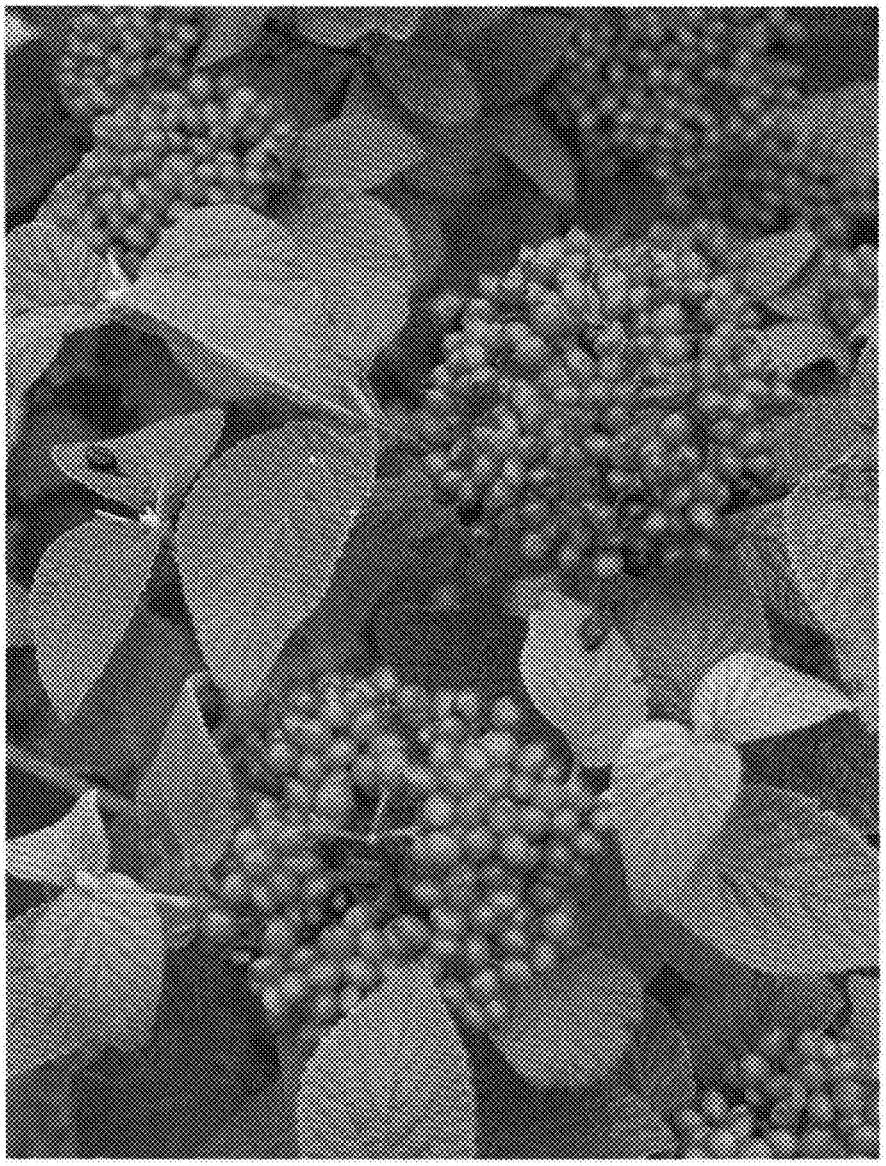

* * * * *